United States Patent
Elings et al.

[11] 4,015,593
[45] Apr. 5, 1977

[54] APPARATUS AND METHOD FOR MEASURING CARDIAC OUTPUT

[76] Inventors: Virgil B. Elings, 5680 Via Salerno, Goleta, Calif. 93017; David T. Phillips, 5107 Calle Asilo, Santa Barbara, Calif. 93111

[22] Filed: Mar. 24, 1975

[21] Appl. No.: 561,650

[52] U.S. Cl. .................. 128/2.05 V; 128/2.05 F; 128/2.1 R
[51] Int. Cl.² ........................................ A61B 5/02
[58] Field of Search .............. 128/2 H, 2 S, 2.05 F, 128/2.05 RQ, 2.05 V, 2.1 R, 2.06 B, 2.1 P, 2.1 Z; 73/194 E, 204

[56] References Cited
UNITED STATES PATENTS

| | | | |
|---|---|---|---|
| 3,405,708 | 10/1968 | Webster, Jr. | 128/2.05 F |
| 3,498,288 | 3/1970 | Max et al. | 128/2.06 B |
| 3,556,082 | 1/1971 | McCullough | 128/2.05 R |
| 3,579,138 | 5/1971 | Harris et al. | 128/2.06 B |
| 3,580,243 | 5/1971 | Johnson | 128/2.06 B |
| 3,587,562 | 6/1971 | Williams | 128/2.1 P |
| 3,618,591 | 11/1971 | Bradley | 128/2.05 F |
| 3,631,438 | 12/1971 | Lewin | 128/2 SW |
| 3,651,318 | 3/1972 | Czekajewski | 128/2.05 F |

OTHER PUBLICATIONS

Wilson, "Proceedings of the 8th Annual 1969 IEEE Region III Convention," Huntsville, Ala., Nov. 19–21, 1969, pp. 45–50.

*Primary Examiner*—William E. Kamm
*Attorney, Agent, or Firm*—Charles H. Schwartz

[57] ABSTRACT

A thermodilution cardiac output computer uses an autobalancing temperature-measuring circuit which adjusts the initial voltage derived from a thermistor and then holds constant the current through the thermistor as the thermistor responds to different temperatures in a blood-injectate mixture. The initial voltage is adjusted to a predetermined constant so that the response from thermistors of different initial resistance is the same. A Wheatstone bridge is not used. Before the temperature measurement, the voltage derived from the thermistor is adjusted to be equal to a predetermined constant either by varying the current through the thermistor or, with a constant current through the thermistor, by varying the gain of the amplifier sensing the voltage across the thermistor. During the temperature measurement this current or gain is held constant. The voltage change derived from the thermistor is integrated in a conventional integrator, and the integration is stopped at the tail of the decay of the temperature-time curve by an automatic timer. This termination point is calculated not as a percentage of the peak value of the curve or at a particular slope of the curve, but as a function of the time of two points high on the decay curve where the artifacts causing undulations in the curve are small compared to the temperature height of the curve. In this fashion, the triggering of the cutoff point by undulations in the curve is avoided.

18 Claims, 11 Drawing Figures

THERMODILUTION CARDIAC OUTPUT COMPUTER

THERMODILUTION CARDIAC OUTPUT COMPUTER

CUT OFF-TIMER 50

Fig. 7d

APPARATUS AND METHOD FOR MEASURING CARDIAC OUTPUT

This invention relates to the thermal dilution method for the measurement of cardiac output and has particular reference to improved methods and apparatus for measuring and integrating the time-temperature curve produced by the dilution of a bolus of cold fluid by blood flow through the heart.

BACKGROUND OF THE INVENTION

The determination of the volume of blood per unit time pumped by the heart is of importance in the diagnosis and treatment of cardiovascular disorders. For critically ill heart patients the physcian must quickly and accurately determine the cardiac output in deciding whether to give the patient medication, perform surgery, or give other immediate treatment. Cardiac output measurements may also be made on a round-the-clock basis in a hospital intensive care unit by nurses or interns with only a minimum of training in the use of each specific instrument. Instruments for this purpose should be capable of accurate and rapid response with a minimum of attention required by the physician in getting the machine stabilized and ready to use. The method must be safe to the patient.

A well-known technique for the determination of cardiac output is the indicator-dilution method, wherein a measured quantity of liquid bearing some indicator is injected in the veins upstream from the heart, and the dilution of this liquid by blood is detected downstream from the heart or downstream from one part of the heart. The greater the flow of blood pumped by the heart, the faster the dilution of the indicator liquid. The injected material is most concentrated immediately after injection, and the concentration drops with the passage of time in an approximately exponential manner. This concentration at a measuring station defines a curve, and the cardiac output is determined by integrating over time the area under this curve. These curves vary in height, duration, and shape from patient to patient. Various indicators are used, including dyes which are detected optically, radioactive isotopes which are detected with radiation detectors, and in the thermodilution method liquids of different temperature from that of the blood, which are detected by thermistor temperature sensors placed in the bloodstream. Thermodilution is an advantageous indicator technique for cardiac output measurement, because the injectate may be completely non-toxic, unlike dyes and radioactive isotopes, and the thermistor measurement of temperature is relatively simple, inexpensive, and safe, and does not require removal of blood samples.

PRIOR ART

Many indicator techniques for cardiac output measurement suffer from a lack of accuracy due to recirculation, since the indicator is not dissipated immediately by the body, but may pass repeatedly through the heart. Thus, much of the patent literature on cardiac output computers is devoted to means of estimating the area of the last portion of the dilution curve so that the measurement can be terminated before the indicator can return to the heart a second time. Recent studies (William Ganz and H. J. C. Swan, *Measurement of Blood Flow by the Thermodilution Technique; Dye Curves, The Theory and Practice of Indicator Dilution*, edited by D. A. Bloomfield, University Park Press, 1974) have shown that this is not a serious problem for thermodilution, since the small volume of injectate is almost completely warmed by the large mass of the body before it can return to the heart. Recent measurements indicate that the recirculation effect in thermodilution is about two per cent. Thus, the direct integration of the thermodilution signal can advantageously be carried much further than in other indicator methods.

The determination of exactly where to end the area integration of the time-temperature curve is a problem. Since the ideal signal begins at the body temperature baseline and returns to it, one might imagine that any sufficiently long period would be satisfactory. Unfortunately, slow drifts in the patient's temperature or in the electronic equipment may cause baseline drifts that lead to large errors if a long integration time is used. One widely marketed commercial instrument used a manually set timer to stop the integration, but this required a skilled operator to inspect a trial dilution curve to determine the optimum time. This instrument did not provide reliable results in the hands of all users and the design has been abandoned by its manufacturer. Another widely used approach is to copy the dye indicator cardiac output computers and cut off the integration early and estimate the area of the unmeasured tail. An example of this approach is to assume exact exponential behavior and detect two points on the curve, such as 60 per cent and 40 per cent of peak. A weighting factor of three is introduced at the 60-per cent point to make up for the missing tail, and the integration is cut off at the 40-per cent point. Others have used the relative slope of the curve to determine a cutoff point.

Typically, the thermodilution curve is not a smooth exponential. Obvious variations occur with the pulse as the heart fills with warm blood; additionally, the curve may be affected by breathing or contain artifacts due to electrical noise sources. Methods based on cutting off the integration when the temperature curve reaches a fixed percentage of its peak value are subject to errors in cutoff time caused by the fluctuations inherent in the signal. These random timing errors introduce an error in the measured area proportional to the size of the signal at the cutoff point multiplied by whatever weighting factor is used. One might hope that cutting off the integral at a fixed percentage of peak when the signal is very small would eliminate this error, but the fluctuations are then larger relative to the signal and so the time errors increase.

Prior art devices for thermal dilution have relied heavily on Wheatstone bridges with a thermistor in one leg of the bridge being responsive to temperature. However, the usual noise rejection benefits of the Wheatstone bridge have not been obtained, since it is impractical to place the other elements of the bridge in the catheter to be inserted into the heart. One important property of the Wheatstone bridge is that when exactly balanced, its response is $V_o(\Delta R)/2 R_o$ where $R_o$ is the thermistor resistance at the baseline temperature, $\Delta R$ is the change in resistance from the baseline resistance $R_o$ due to a change in temperature $\Delta T$, and $V_o$ is the bridge excitation voltage. Since thermistors vary their resistance with temperature according to the relation $R = A \exp(B/T)$, the Wheatsone bridge circuit eliminates dependence on the constant A, which is determined by the exact dimensions of the thermistor, because $\Delta R/R_o$ is independent of A. This leaves only the constant B, wich is determined by the material from which the thermistor is constructed. The constant B is almost the same for thermistors produced by the same manufacurer, while the constant A varies from thermistor to thermistor. It is advantgeous to have a circuit which does not require specially calibrated thermistors.

To use the bridge circuit to accurately measure temperature changes, it is necessary to carefully adjust it for zero output at the initial temperature. This normally requires an exacting manual adjustment by the physician just at the time he is least interested in thinking about the instrument. An electromechanical servomechanism might be employed for this task, but they are expensive and subject to wear; thus, they have not been used commercially. Attempts have been made to simply subtract the baseline error of a bridge only approximately balanced, but a careful analysis shows that the sensitivity of the bridge circuit changes when it is off balance, so accurate results cannot be obtained without carefully balancing the bridge.

SUMMARY OF THE INVENTION

We have discovered a method of measuring temperature changes of the blood which does not use a Wheatstone bridge. Instead, we have an autobalance circuit that delivers a steady current I to the thermistor during the measurement such that the initial thermistor voltage is set to a predetermined value, $V_o$. The feedback circuit which sets the current automatically creates a zero baseline condition without the need for a human operator to balance the circuit. Since $IR_o$ is set to $V_o$, $I = V_o/R_o$; thus, the change in signal voltage produced during the measurement is $I(\Delta R) = V_o(\Delta R)/R_o$, which provides the same advantage as the Wheatstone bridge in that uncalibrated thermistors may be used, since the response is independent of the initial resistance of the thermistor. In addition to providing automatic balance and the use of uncalibrated thermistors, the circuit has further advantages in that it can be made completely symmetric for the highest noise rejection. This noise rejection allows the circuit to operate well with a very low current I through the thermistor as required for patient safety. Also, the circuit can operate with large resistors in series with the thermistor to protect the patient from accidental electrical shock.

We have also discovered a method of electrically integrating or measuring the area under the temperature-time curve that is more accurate than present methods. We select a region high on the curve where the temperature response is high compared to the noise and artifacts that disrupt the curve. We use the properties of the curve in this region to determine a later time of cutoff of the integrating or measuring process. By selecting a time of cutoff rather than a cutoff when the curve falls to a certain fraction of its peak value, we avoid triggering the cutoff by the fluctuations in the curve, which is so common in the prior art devices. While our time of cutoff can be adjusted to any practical point, we prefer a cutoff where the curve is in the area of five to ten per cent of peak. This region of cutoff eliminates most of the error due to baseline drift. A small weighting factor may be used to correct for the missing tip of the tail of the curve. We terminate the integrating of the area under the curve at a time determined by previous functional properties of the curve rather than at a certain height of the curve.

DESCRIPTION OF THE FIGURES

Various objects, advantages, and features of the invention will be apparent in the following description and claims, considered together with the drawings forming an integral part of this specification and in which:

Figure 1:
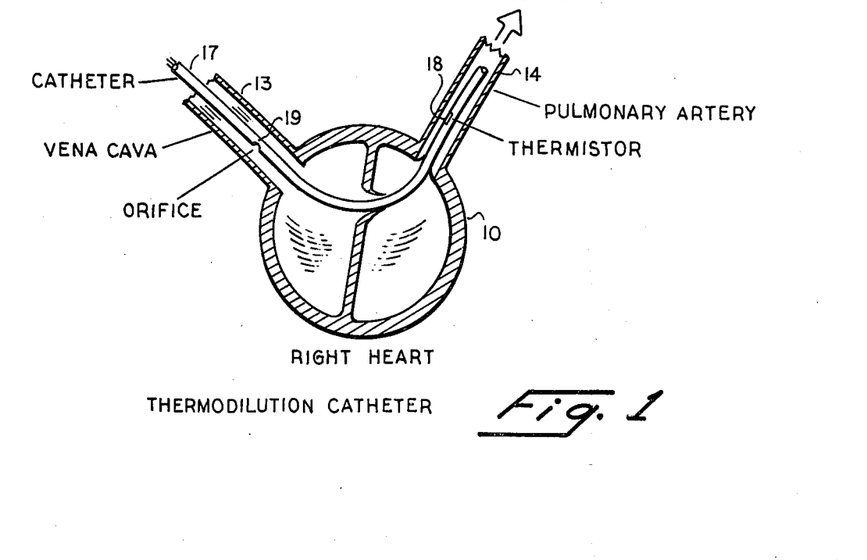
FIG. 1 is a diagram of the right heart of a human being, showing a catheter inserted through the right heart, which includes a thermistor for carrying out the invention.

Referring to FIG. 1 there is illustrated the right part of a human heart 10. A large vein, vena cava, 13 leads to the right heart 10, and an artery 14 leads to the lungs. A cut is made in the vein 13, and a catheter 17 is inserted into this cut and passed along the vein 13 toward the right heart 10 and through the right heart 10 to a short distance beyond. Any suitable type of catheter may be used, and the type embodying a balloon may be used so that the balloon can be inflated to float the catheter tip up the vein and through the right heart to the position illustrated. Disposed in the catheter 17 is a thermistor 18, and this thermistor is insulated from the blood by a thin film which allows the thermistor to follow very closely the temperature of the bloodstream at its location. The catheter 17 is a complex of passages and wires in flexible form, and at a point 19 an orifice is cut to the outside of the catheter, and it is at this point that liquid is injected into the bloodstream from the far end of the catheter (not shown). These catheters are well-known in the medical field and, accordingly, are not shown or described in detail.

A measured quantity of cold liquid is injected into the bloodstream at point 19 of FIG. 1, and, generally, this quantity is on the order of ten cc of a compatible liquid, such as saline solution or glucose solution, which has been cooled to about 1° C. This injectate is rapidly introduced into the bloodstream and is thoroughly mixed by the action of the right heart 10. After a flow-time delay, this mixture reaches the thermistor 18, which then responds to create a voltage, and this voltage curve form is shown in FIG. 2.

Figure 2:
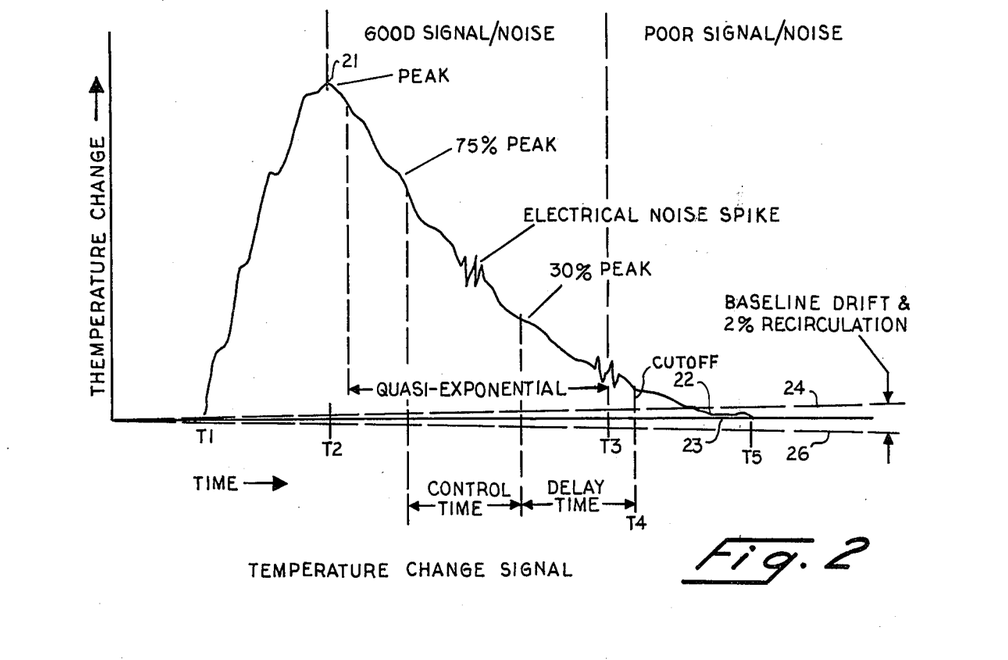
FIG. 2 is a diagram of a typical temperature-time curve, showng the response of a thermistor to an injected liquid differing in temperature from the body temperature of the patient and indicating the part of the curve used in the invention for determining the time for terminating integration in another part.

Referring to FIG. 2, it will be noted that the time axis for recording the temperature is the horizontal axis and the temperature axis is the vertical axis of the graph of FIG. 2. The first flow of mixture is detected at time T1 on the graph, and the mixture of injectate and blood flows as a mass through artery 14 to the thermistor 18 to cause a peak voltage indication at 21. Thereafter, the curve falls slowly until about the 90-per cent area, whereupon the curve steepens; and beyond the 90-per cent mark on the decay portion of this curve, the curve is approximately exponential. It will be noted in FIG. 2 that the rising part of the curve from T1 to peak at 21 is wavy and not smooth due to the effect of heartbeats and breathing on the temperature of the patient, etc. The same irregularity persists on the decay portion of the curve from the peak 21 to the tail of the curve at 22. It will be noted, however, from time T3 to the tail of the curve 22 that the undulations in the curve are substantial with respect to the vertical height of the curve, and thus any attempt to terminate the reading or integration of the curve as a percentage of peak would be extremely inaccurate as to the point of cutoff.

In order to get an accurate determination of cardiac output or the flow rate of the heart 10, it is necessary to measure the area under the curve, which measurement is usually referred to as an integration. Ideally, the curve must be integrated between a base line 23 and the uprising portion from T1 to 21 and the decay portion from 21 to 22. In actual practice, however, this base line 23 is not stable and may vary from above the nominal base line 23, as shown by the dotted line 24, or may be below the nominal base line, as shown by the dotted line 26. If, therefore, it is attempted to integrate 100 per cent of the curve, this might be impossible in the event of a drift below nominal base, as shown by the line 26, and the apparatus would continue to integrate long after the curve was terminated in fact. It is for this reason, therefore, that in accordance with our invention we cut off a portion of the tail of the curve to stop the integration. The cutoff portion is from time T4 to time T5, and the useful cutoff area is part of the poor signal/noise region shown in FIG. 2. This cutoff portion is at the tail of the curve and we have used with success a time delay cutoff at approximately 10 per cent of peak. If desired the area of this cutoff portion may be estimated, and an electrical factor added, based on the area of the curve already measured, to give a simulated 100 per cent integration.

In carrying out our invention of terminating the integration at a definite time period rather than at a percentage of peak, we presently prefer to use two points that are high up on the decay curve, which extends from 21 to 22. The time between these two points establishes a control time period. This region of high response is less affected percentage-wise by the undulations in the curve than is the lower portion of the decay curve. This region of good signal-to-noise ratio extends from peak T2, to T3, which is about 20 per cent of peak. We prefer to utilize the quasi-exponential part of this T2-to-T3 region, and this starts at about 95 to 90 per cent of peak, depending on the particular curve. The second point is from 50 to 20 percent of peak. Presently, the first point in this T2-to-T3 region which we prefer is 75 per cent of peak, and the second point which we prefer is 30 per cent of peak. We have devised apparatus which senses and holds the peak 21, and when the decay curve drops to 75 per cent of peak, an electronic time-measuring device is started. When the curve decays to the 30 per cent point, this time-period measurement is then stopped. The timing period is designated "control time" in FIG. 2. The time thus determined between 75 and 30 per cent of peak is then multiplied by a suitable factor that will be used in a cutoff circuit to terminate the integration after thirty per cent in the poor signal-to-noise region, namely, T3 to T5, which is approximately from 20 to 2 per cent.

Figure 3:
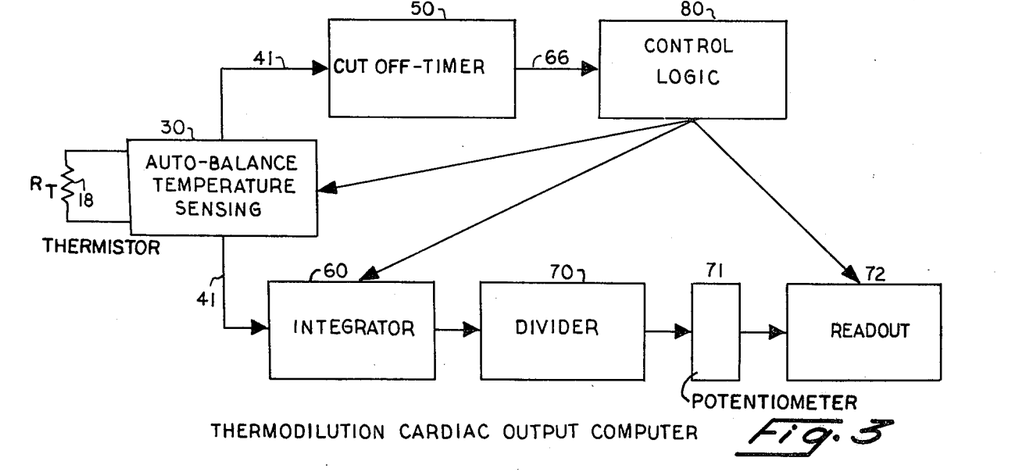
FIG. 3 is a schematic block diagram of the circuit components for carrying out the measurement of cardiac output and showing in block form the novel circuits of the invention.

Referring to FIG. 3, there is illustrated in block diagram a circuit for carrying out the integration described in FIG. 2, as well as carrying out our improved temperature-sensing function and completing the readout function for the entire apparatus. At the left in FIG. 3 is shown the thermistor 18 connected to a temperature-sensing circuit 30, which feeds its output into a cutoff timer 50, as well as an integrator 60. The temperature-sensing circuit 30 initiates the integration of integrator 60, and the cutoff timer 50 acts through a logic circuit 80 to stop the integrator 60 at the selected time along the tail of the curve of FIG. 2. The output of the integrator is fed into a divider 70, and its output is controlled by a potentiometer 71, which reflects the differential in temperature between the patient and the injectate, and this modified output is then fed into a readout mechanism 72, which can be any type of meter, but we presently prefer a digital type of meter. The integrator 60 is old and well-known in this art, and the divider is also old and well-known, together with the potentiometer 71 and the readout 72. The novel parts of this circuit provided in accordance with the invention are the temperature-sensing circuit 30 shown in FIGS. 4 and 5 and the cutoff timer 50 shown in FIG. 6.

Referring to FIG. 3, the control logic 80 is used as a sequencer and resetter. It initiates the circuit operations of the temperature sensor 30, the integrator 60, and the readout 72, and controls the sequence of operation. At the end of the measurement it discharges capacitors and resets these circuits, so that they can be rid of any prior charges and voltages so that the readout will not reflect any prior test measurement.

Figure 4:
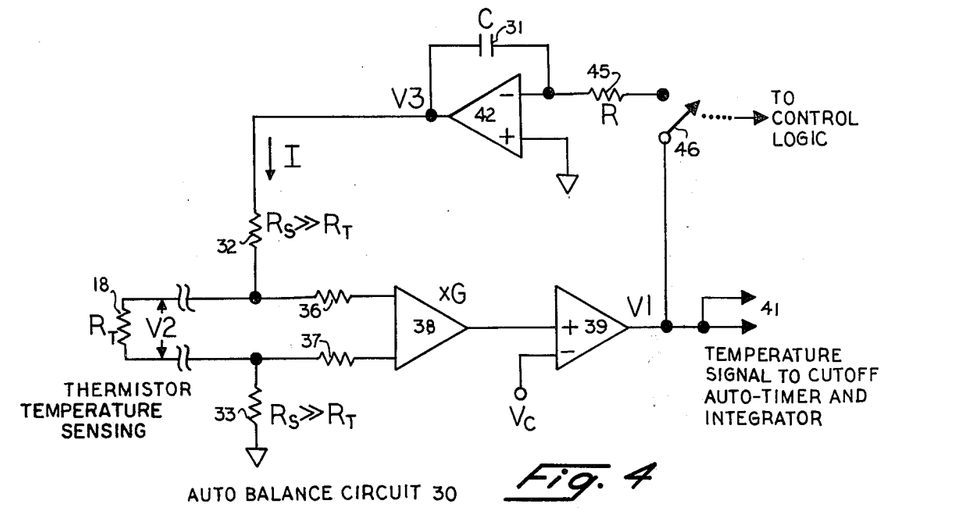
FIG. 4 is a circuit diagram of a presently preferred form of the temperature-sensing circuit, embodying the invention as shown in block form on FIG. 3.

Referring to FIG. 4, there is illustrated in detail the temperature-sensing circuit 30. Current flows through a buffer resistor 32, through the thermistor 18, and a second buffer resistor 33. The flow of current through the thermistor 18 causes a voltage drop V2, and this voltage difference is fed through isolation resistors 36 and 37 to a differential amplifier 38. The output of the differential amplifier 38 is fed into a second differential amplifier 39 in which a reference voltage $V_c$ is subtracted. Connected to this amplifier 39 are conductors 41, which pass this voltage on to the cutoff auto-timer 50 and the integrator 60 as shown in FIG. 3. The amplifier 39 is connected to a switch 46, and when closed current flows through a resistor 45 to an integrating amplifier 42. The output of this amplifier is connected to the resistor 32, forming a closed loop when switch 46 is closed. Amplifiers 38, 39, and 42 are powered and hence act as a source of current and voltage.

Switch 46 is closed before the masurement and is opened to make the cardiac output measurement. With switch 46 closed, the voltage V1 from amplifier 39 produces a current through resistor 45, which is integrated on a capacitor 31 connected in parallel with the amplifier 42, thereby decreasing the voltage V3 applied to resistor 32. This decreases the current through the thermistor 18, thereby decreasing the voltage drop V2 across the thermistor 18. This, in turn, decreases the voltage output of amplifier 38 and the voltage V1.

This auto-balancing process continues until the voltage V1 is at or near zero. The time constant associated with this auto-balancing is given by the product of the value of the resistor 45 and the value of the capacitor 31 and is typically a few seconds. When the circuit is in equilibrium or balance, the voltage drop V2 across the thermistor 18 is equal to $V_c$ divided by the gain G of the amplifier 38. When the thermistor is at room temperature and inserted into the bloodstream prior to the test, this change in temperature causes a big change in thermistor resistance. With switch 46 closed and such a change occurring or if thermistor 18 is replaced by one of a different nominal resistance, the circuit will automatically adjust itself or auto-balance unitl the voltage drop across the thermistor is agian $V_c/G$, a constant. It will be appreciated that the circuit of FIG. 4 does not have a Wheatstone bridge.

During the measurement of cardiac output, the voltage V3 acts, together with resistors 32 and 33, as a constant current source. This is because the values of the resistors 32 and 33 are large compared to the change in resistance of the thermistor 18 during the measurement of cardiac output. Typically, resistors 32 and 33 are on the order of a megohm, and the change in resistance of the thermistor is typically on the order of one kilohm. In effect, the overall resistance is so great that the change in resistance of the thermistor is negligible and the current flow remains constant. Resistors 36 and 37 may be of megohm size.

When switch 46 is opened immediately preceding the measurement, current can no longer flow through resistor 45 and the voltage output V3 of the integrating amplifier 42 remains constant or holds at its value which it had immediately before the switch 46 was opened and the current through the thermistor now remains constant. As the temperature and, therefore, the resistance of the thermistor 18 now varies, the voltage drop across the thermistor 18 will change. This voltage will be amplified in amplifiers 38 and 39 and produce a new voltage V1, which is not zero. This voltage is fed through conductors 41 to the timer and integrator. The response of the voltage V1 to a change in resistance $\Delta R$ of the thermistor 18 is given by the product of the current through the thermistor multiplied by the change in resistance $\Delta R$, and the gain G of amplifier 38: $V1 = I\Delta RG$. It is noted that the sensitivity is proportional to I. The constant current I is equal to $V_c/(GR_o)$, where $R_o$ is the resistance of the thermistor immediately before switch 46 was opened, so $V1 = V_c \Delta R/R_o$. The voltage response of the circuit in FIG. 4 is, therefore, proportional to the fractional change in the resistance of the themistor 18, similar to the response of a balanced Wheatstone bridge. Due to the properties of thermistors, V1 is proportional to the change in temperature of the thermistor, independent of the initial resistance $R_o$ of the thermistor, for the small temperature changes involved in the thermodilution technique. The temperature-sensing circuit in FIG. 4, therefore, automatically sets its sensitivity and base line when switch 46 is closed by adjusting the current through the themistor and then holds this sensitivity constant during the measurement when switch 46 is open.

It will be noted in FIG. 4 that the thermistor 18 is completely surrounded by large resistors, being resistors 32, 33, 36, and 37. Therefore, if the electrical insulation on the thermistor 18 breaks down or if the insulation on its leads inside the catheter break down or if there is an electrical malfunction in amplifiers 38 or 42, the available current will not be sufficient to cause any malfunctioning of the patient's heart. This protection of the patient is in sharp contrast with the Wheatstone bridge commonly used in the prior art devices, where one thermistor lead is usually attached directly to the circuit ground and dangerous currents could be injected into the heart of the patient by breakdown of insulation on the electrical components.

The circuit in FIG. 4 is symmetric about the two leads of the thermistor 18 if the resistors 32 and 33 have equal values and if the resistors 36 and 37 have equal values. Any voltages produced equally on both leads, such as 60-cycle pickup noise from the patient or adjacent equipment, will be completely cancelled by the circuit and will not appear in the voltage V1. This excellent common-mode rejection allows the circuit to operate at very low thermistor currents of typically six microamps and with an upper limit of ten microamps under faulty conditions.

It will be appreciated that the functions of amplifiers 38 and 39 could be combined into a single amplifier. It will also be appreciated that the integrating amplifier 42 might be used to control other types of current sources.

Figure 5:
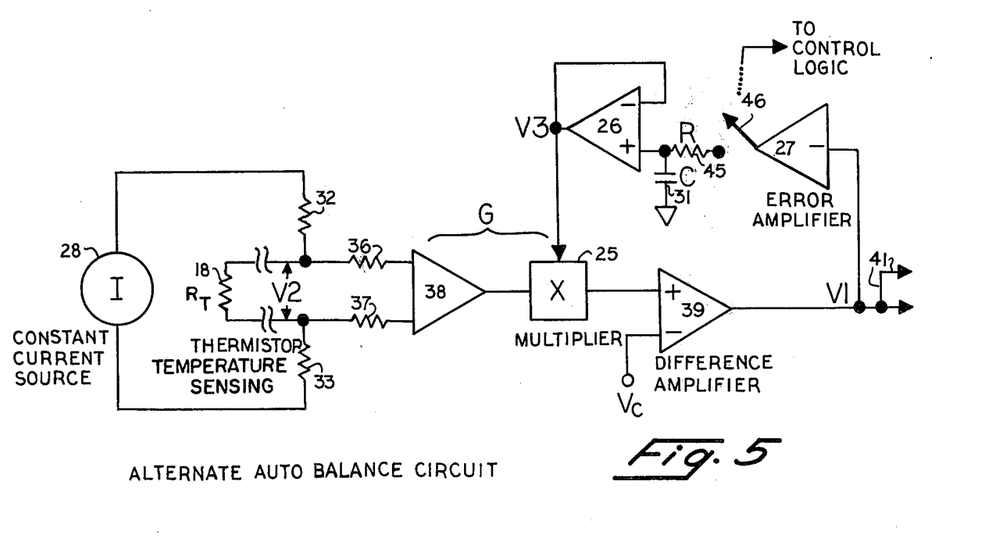
FIG. 5 is a circuit diagram of a modified form of the temperature-sensing circuit.

FIG. 5 shows an alternative form of the auto-balance apparatus, the presently preferred embodiment being shown in FIG. 4. In this modified circuit, a multiplier 25 is interposed between the amplifiers 38 and 39. In FIG. 5 the thermistor 18 is energized by a constant current source 28 of fixed current magnitude I, and thus voltage V2 equals IR, where R is the thermistor resistance. The resistors 32 and 33 serve as before to limit the current in case of failure of some component. The combined gain G of the amplifier 38 and the multiplier 25 is controlled by the voltage V3 at the output of an amplifier 26. A predetermined constant voltage $V_c$ is subtracted from the amplified thermistor voltage GIR by the difference amplifier 39 to produce voltage V1. This voltage is transmitted to an inverting amplifier 27. Before the measurement, during the auto-balance period, switch 46 is closed, and so voltage V1 is amplified by the inverting error amplifier 27 and the output of amplifier 27 charges capacitor 31 through resistor 45. The voltage on capacitor 31 is maintained by integrating amplifier 26 and is transferred to the multiplier 25. This feedback loop adjusts the gain G so that V1 is zero. Thus, $GIR_o$ is set equal to $V_c$. During the temperature measurement the switch 46 is opened and the voltage on capacitor 31 is left constant, fixing the sensitivity of the circuit. Thus, changes in thermistor resistance produced by temperature changes lead to temperature signal voltage V1 equal to GIR - $V_c$, which is equal to $V_c \Delta R/R_o$ as desired. It will be appreciated that amplifier 26 of FIG. 5 holds the gain of multiplier 25 constant in the same fashion that amplifier 42 of FIG. 4 held the current constant. Since the signal V1 is dependent on the product GI, similar results may be obtained by controlling either I as in FIG. 4 or G as in FIG. 5.

Figure 6A:
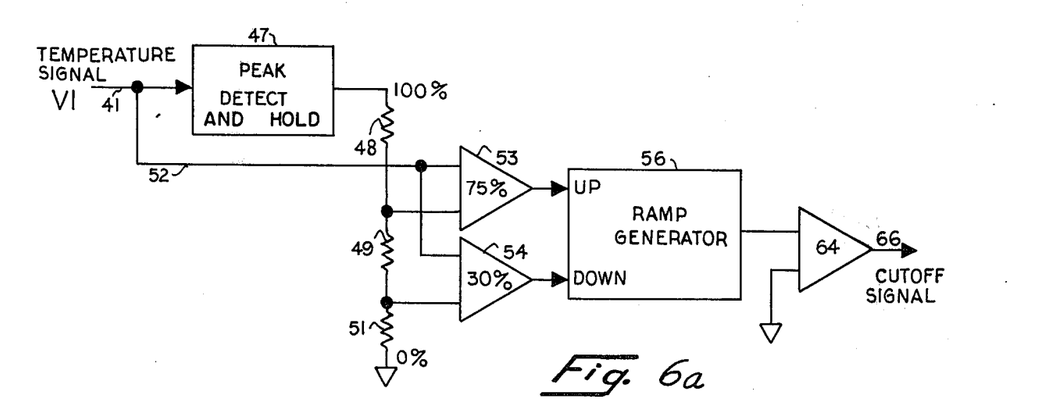
FIG. 6(a) is a circuit diagram showing a cutoff timer embodying the invention, also shown in block form in FIG. 3.
Figure 6B:
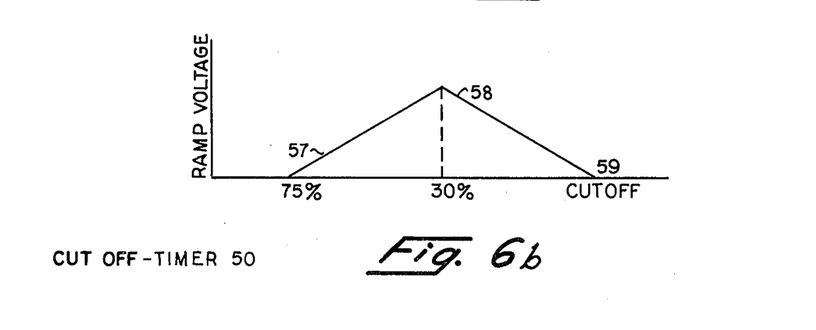
FIG. 6(b) is a waveform used in explanation of FIG. 6(a)

Referring now to FIG. 6(a), which shows the cutoff auto-timer 50 of FIG. 3, the signal V1 from the temperature-sensing circuit of FIG. 4 appears at the left in conductor 41. This signal represents the temperature change of the thermistor 18 of FIG. 4 during measurement of cardiac output. This voltage is fed into a peak detector 47, which detects the peak 21 of the curve of FIG. 2 and thereafter maintains a voltage at that peak voltage and delivers it through a voltage divider, including resistors 48, 49, and 51, which can define any percentage of the peak voltage desired, including the peak itself, and in the illustration of FIG. 6 this is at the 75-per cent point of peak and at the 30 per cent point of peak. Branching from the input lead 41 is a conductor 52, which leads to two comparators 53 and 54. Comparator 53 is connected to the 75-per cent point on the voltage divider. When the signal from lead 41 reaches 75 per cent of peak, this is instantly recognized by the comparator 53, which sends a signal to a ramp generator 56, which develops a ramp-up voltage shown by the line 57 below the circuit diagram in FIG. 6(b). When the voltage being supplied by conductor 41 reaches 30 per cent of peak, this is recognized by the comparator 54, which then sends a second signal to the ramp generator 56, causing a declining ramp 58. When this ramp voltage 58 reaches the zero mark at point 59, this point is detected by a zero detector 64, which then sends a signal over conductor 66 to logic 80 and the integrator 60 of FIG. 3, thus stopping the integration. It will be recognized that the resistors 48, 49, and 51 may be properly selected to provide any percentage of peak that is desired for presenting one or more signals to the comparators 53 and 54. It will be further recognized that the ramp generator may be of conventional type such as charging and discharging an R-C circuit, with the charging and discharging currents appropriately selected. The zero point 59 on the ramp 58 is in the tail region of the curve as shown in FIG. 2, and this zero point is selected by adjusting the ramp generator 56 to discharge at any selected multiple of the time period from the 75-per cent-of-peak point to the 30-per cent-of-peak point.

Figure 7A:
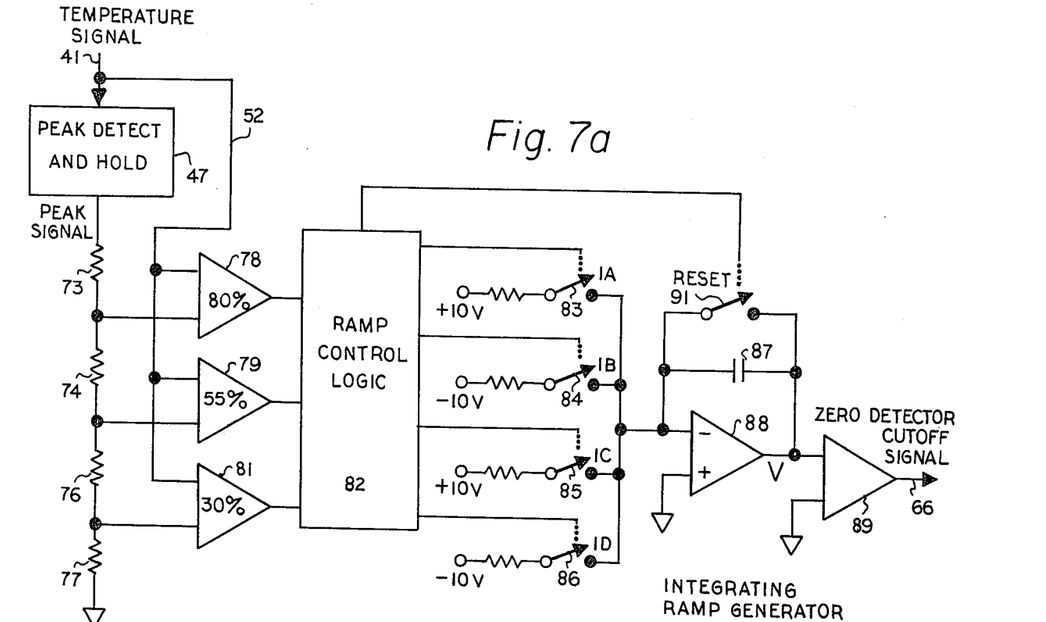
FIG. 7(a) is a circuit diagram of a modified form of cutoff timer.

Shown in FIG. 7(a) is a modified form of autotimer using three points on the decay curve to establish a time period to control the cutoff of the integrator 60. The same peak detector 47 is used as in FIG. 6, but this voltage is divided to give three points and these are shown for illustrative purposes as 80 per cent, 55 per cent, and 30 per cent of peak respectively. Connected to the peak detector 47 in series are four resistors 73, 74, 76, and 77, producing voltages between them to which are connected comparators 78, 79, and 81. These comparators are also connected to the thermistor output by conductor 52 and recognize the respective percentages of peak, whereupon they send signals to a ramp control logic circuit 82, which activates switches 83, 84, 85, and 86, which control charging and discharging currents IA, IB, IC, and ID, to a capacitor 87. This capacitor is connected in parallel with an amplifier 88 to form an integrator, and this output connects to a zero detector 89 to deliver the cutoff signal to the control logic 80 of FIG. 3, which in turn stops the integrator 60.

Figure 7B:
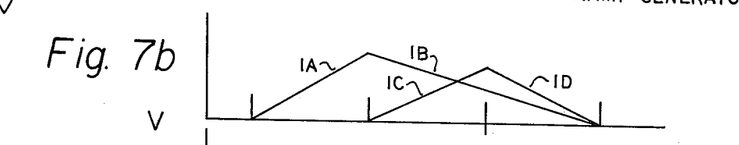
FIG. 7(b), (c), and (d) are waveforms used in explanation of FIG. 7(a).
Figure 7C:
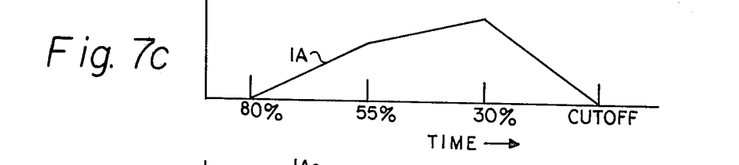
Figure 7D:
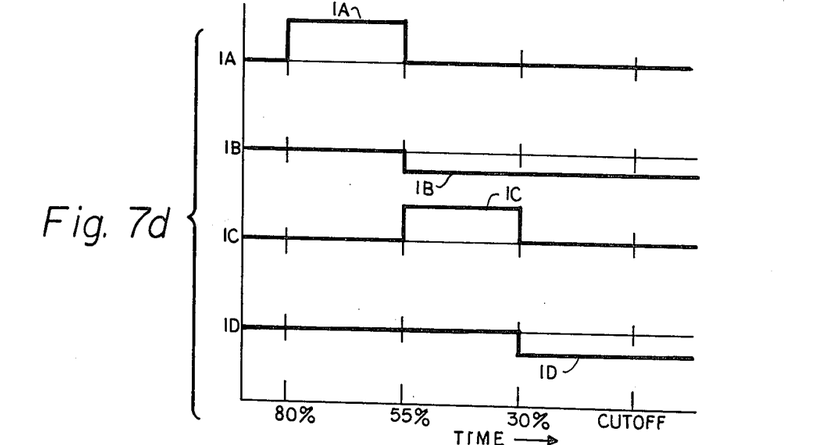

The operation of FIG. 7(a) is as follows: When the comparator 78 recognizes eighty per cent of peak, it sends a signal to logic 82, which closes switch 83 clockwise to cause a current IA to flow to capacitor 87. This causes a charge to build up as shown in FIG. 7b and FIG. 7c. The time periods for the current flows IA, IB, IC, and ID are also shown on FIG. 7(d). When the thermistor signal reaches 55 per cent of peak, comparator 79 sends a signal to logic 82, which opens switch 83 and closes switch 84. This causes a discharge current IB to flow from th capacitor 87. This voltage decreases is shown in FIG. 7b and the negative current flow in FIG. 7d. At the same time logic 82 closes switch 85 to cause a charging current IC to flow, which would tend to charge capacitor 87, but which actually flows in part through switch 84 and its associated resistor. When th thermistor signal reaches 30 per cent of peak, comparator 81 sends a signal to logic 82, which opens switch 85 and closes switch 86, so that a discharge current ID flows from capacitor 87. At this time two discharge currents IB and ID are flowing. When the capacitor reaches zero voltage, this is recongnized by the zero detector 89, which sends a signal to control logic 80 (FIG. 3), which then stops the integrator 60 of FIG. 3.

The algebraic sums of the current flows of FIG. 7b are shown in FIG. 7c. At a suitable time after the zero cutoff point is reached by capacitor 87, the ramp logic 82 closes a switch 91 to reset the integrator 87-88 and to open all switches 83, 84, 85, and 86.

Using three or more points on the curve permits the cutoff time to be averaged over several independent determinations, reducing the influence of spurious undulations in the signal. The ramp up currents IA and IC may be at different rates, and the discharge currents IB and ID may be at different rates.

OPERATION

The commonly used formula for cardiac output is as follows:

$$\text{Cardiac output} = (T_B - T_I) \times C$$

where
Vol. = volume of injectate;
$T_B$ = temperature of the blood before injection
$T_I$ = temperature of the injectate before injection
$C$ = a constant which contains the specific heats of the blood and injectate, the volume of the injectate, a correction factor for the particular catheter which is used.

In adapting this formula to FIG. 3, the temperature of the blood and the injectate and the constant C are dialed into potentiometer 71.

The temperature-sensing circuit 30 with switch 46 in FIG. 4 closed automatically adjusts the current through the thermistor 18 so that the voltage drop across the thermistor 18 is $V_c/G$, a constant which is independent of the thermistor being used. This auto-balancing adjusts the sensitivity of the circuit so that during the measurement the response from the circuit will be proportional to the temperature change of the thermistor and independent of the initial resistance of the thermistor. The operator opens the switch 46 either manually or electronically and within a short period of time injects a liquid out of the orifice 19 of catheter 17 of FI. 1. This liquid may be 10 cc of a five-per cent dextrose solution at a temperature between 0° C. and 27° C. The blood flow is to the right, which causes the injectate and the blood to mix in the right heart 10, and this mixture of cold liquid and warm blood flows to the thermistor 18, whereupon the thermistor changes in resistance.

Referring to FIG. 4 with switch 46 open the current through the thermistor 18 is held constant at the value it had immediately before the switch was opened. The change in voltage across the thermistor produces a response V1 which is proportional to the temperature change, as shown in FIG. 2. The first part of the mixture to reach the thermistor 18 initiates the curve at T1; the peak of the mixture is registered at 21 on FIG. 2, and thereafter the decay of the curve continues to point 22.

The differential amplifier 38 eliminates electrical noise which may be picked up on the thermistor leads from the vast array of electrical equipment found in hospitals. Even when external noise sources have been eliminated, there still remains troublesome variations in temperature, which are present in the body. The breathing cycle causes periodic temperature variations estimated by some to be typically 0.02° C., and even more with certain irregularities in circulation. There are also sudden changes of temperature as fresh blood fills the heart with each beat, so that the falling edge of the curve is a series of steps, or undulations. In extremely sick patients there is frequently a pronounced baseline drift as shown by lines 24 and 26 of FIG. 2. There also may be electrical drifts in the circuitry shown by these lines 26 and 24. The present invention, by using a time period of cutoff, eliminates these undulations or steps or variations in the curve as triggering factors to determine the point of cutoff T4 of the integration.

Referring now to FIG. 6, when a selected point on the decay curve is reached by the voltage supplied by the thermistor 18, this is recognized by the comparator 53, which triggers the ramp generator 56 to build the upramp 57 of FIG. 6. When the curve decays further, for example, to the 30-per cent point, then the second comparator 54 triggers the ramp generator 56 to cause a down-ramp 58, and when this ramp reaches zero, then this is detected by the zero detector 64, which sends a signal to the integrator 60 of FIG. 3 via the control logic 80. This causes the integration to cease, whereupon a signal corresponding to the area under the curve of FIG. 2 from T1 to T4 is transmitted to the divider 70, which inverts the signal and that output is delivered to the potentiometer 71, which dials in the multiplier for the difference in body and injectate temperatures and the constant C in the equation, and the resultant is converted to a visual indication in the readout 72, which may be any type of voltmeter but is preferably a digital meter.

The cutoff time is determined in advance up high on the curve of FIG. 2 where the undulations and noise are small compared to the temperature measurement. In this way the minimum effect of these undulations is achieved in selecting the cutoff time period. The inaccuracies due to baseline drift are minimized by cutting off the tail of the curve at T4, as shown in FIG. 2. In this fashion we are able to integrate substantially the entire curve with a minimum error in the cutoff point. The small area which is cut off from T4 to T5 can be estimated, and a correction can be made to the measured area of FIG. 2. If the timing happens to cut off the inegration at approximately 10 per cent of peak becuase of the shape of the curve, more than ninety per cent of the area is integrated, and the integration will aproximate 95 per cent of the area. If the cutoff is at five per cent of peak, then about ninety-eight per cent of the area under the curve will be integrated. Thus, substantially all of the area is integrated.

Referring to FIG. 4, it will be noted that the gain of amplifiers 38 and 39 is fixed, and the reference voltage $V_c$ is fixed. The feedback loop 46, 45, 42, and 32 is used to adjust the current flow through the thermistor 18 prior to meansurement. In FIG. 5 the current flow from 28 is fixed and constant and $V_c$ is constant. The gain is the variable controlled by feedback loop 27, 46, 45, and 26. The multiplier 25 and amplifiers 38 and 39 can be considered as a single variable amplifier.

We have determined that the reference voltage should not be varied as a "baseline subtraction" while keeping the current and gain constant, since the temperature sensitivity of the circuit would then vary from thermistor to theremistor and give erroneous readings.

The cutoff instant can be timed from the end of the time period measured (for example, the 30-per cent point), from the beginning of the time period (for example, the 75-per cent point), or from peak or any other point on the decay portion of the curve. The delay from the timing point is a function of the measured times.

As used in this specification the terms "current source," "voltage source," and "electrical power source" have the following meanings:

A. A current source provides an output current which does not change as the output voltage and load resistance vary.

B. A voltage source provides an output voltage which does not change as the output current and load resistance vary.

C. An electrical power source provides output voltage and current which may vary with the load resistance.

The methods set forth in this dislcosure may be accomplished by analog or digital computing devices rather than the particular circuits shown.

We have described our invention with respect to presently preferred embodiment thereof as required by the rules of the Patent and Trademark Office. The embodiments disclosed, therefore, are merely illustrative of our invention and are not definitive. Various modifications and variations will occur to those skilled in the art, and we include within the scope of the following claims all such variations and modifications that fall within the true spirit and scope of the invention.

We claim:

1. A method of initially balancing and thereafter operating a circuit for measuring the temperature change of a blood-injectate mixture and with the temperature change measured using a thermistor energized by an alternating or direct current source and in which the current is held constant during measurement, including the following steps adjusting the initial sensitivity of the circuit prior to measurement of blood-injectate temperature to produce an initial amplified thermistor voltage ($GIR_o$) equal to a predetermined constant; and holding constant the circuit sensitivity during temperature change measurement of the blood-injectate mixture by the thermistor whereby changes in the amplified thermistor voltage which occur due to the temperature changes of the blood-injectate mixture are indepded of the inital thermistor resistance and dependent only on the temperature change and the material constant (B) of the thermistor.

2. The method of claim 1 wherein the step of adjusting the initial sensitivity of the circuit includes initially adjusting the current source energizing the thermistor to produce the thermistor voltage ($GIR_o$) equal to the predetermined constant and wherein the step of holding constant the circuit sensitivity includes holding the current energizing the thermistor constant during measurement.

3. The method of claim 1 wherein the step of adjusting the initial sensitivity of the circuit includes initially adjusting the amplification of the amplified thermistor voltage to produce the thermistor voltage ($GIR_o$) equal to the predetermined constant and wherein the step of holding constant the circuit sensitivity includes holding the amplification constant during measurement.

4. An autobalance circuit for sensing the temperature changes of a flowing blood-injectate mixture for use in equipment for measuring cardiac output by thermal dilution, the autobalance circuit including a thermally variable resistor for detecting the temperature of the blood-injectate mixture in accordance with the resistance of the variable resistor, a source of current coupled to the variable resistor for producing a voltage drop across the variable resistor in accordance with the resistance of the variable resistor, first means coupled to the variable resistor and responsive to the change in the voltage drop across the variable resistor for producing an output voltage in accordance with the change in the voltage drop across the variable resistor, and wherein the first means includes a source of reference voltage and a means for subtraction coupled to the source of reference voltage and to the voltage drop across the variable resistor for producing the output voltage from the first means in accordance with subtraction of the source of reference voltage from the voltage drop across the variable resistor, a feedback loop coupled to the first means and responsive to the output voltage from the first means for producing a feedback signal having a value for providing a zero output voltage from the first means to initially balance the circuit and with the feedback loop including means for decoupling the output voltage from the first means to the feedback loop after the production of te zero output voltage from the first means and with the feedback loop including a holding control for maintaining the same value for the feedback signal after the output signal from the first means is decoupled for providing after the initial balance an output signal from the first means only in accordance with changes in the voltage drop across the variable resistor.

5. The autobalance circuit of claim 4 wherein a nonvariable resistor is connected in series with the thermally variable resistor to limit current flow to a few microamperes.

6. The autobalance circuit of claim 4 wherein circuit-limiting resistors are disposed symmetrically in series with the thermally variable resistor and the first means is connected through symmetrical isolation resistors to the thermally variable resistor.

7. The autobalance circuit of claim 4 wherein the feedback signal is coupled to the source of current for initially varying the current to produce the zero output voltage from the first means to initially balance the circuit and with the holding control thereafter maintaining the source of current at a constant value after the output voltage from the first means is decoupled from the feedback loop.

8. The autobalance circuit of claim 17 wherein the first means includes means for providing variable gain and with the feedback signal coupled to the first means for varying the gain of the variable gain means to produce the zero output voltage from the first means to initially balance the circuit and with the holding control thereafter maintaining the variable gain means at a constant level after the output of voltage from the first means is decoupled form the feedback loop.

9. The autobalance circuit of claim 4 additionally including second means coupled to the first means and responsive to the output signal from the first means for integrating the level of the output signal from the first means relative to the passage of a calculated period of time for providing a measurement of cardiac output in accordance with the change of temperature of the blood-injectate mixture.

10. Apparatus for terminating the integration of a time-temperature curve for use in equipment for measuring cardiac output by thermal dilution and with the time-temperature curve represented by a varying voltage having an initial rising portion to a peak and a decay from the peak, the apparatus including first means responsive to the varying voltage for detecting and holding the peak voltage, second means coupled to the first means and responsive to the peak voltage and to the varying voltage for detecting when the varying voltage decays to a first predetermined percentage of the peak voltage, third means coupled to the first means and responsive to the peak voltage and the varying voltage for detecting when the varying voltage decays to a second predetermined percentage of the peak voltage lower than the first predetermined percentage, fourth means coupled to the second and third means and responsive to the detection by the second and third means for producing a cutoff signal which is time delayed after the detection by the third means in accordance with the time interval between the detection by the second and third means; and fifth means coupled to the fourth means and responsive to the cutoff signal and the varying voltage for integrating the varying voltage relative to time and for terminating the integration in response to the cutoff signal.

11. The apparatus of claim 10 wherein the production of the cutoff signal is time delayed a period of time substantially equal to the time interval between the detection by the second and third means.

12. The apparatus of claim 10 wherein the fourth means includes a ramp generator for generating a ramp signal having a direction in accordance with the inputs to an up and a down input and with the detection by the second means providing an input to the up input of the ramp generator for generating a ramp signal in an up direction until the detection by the third means provides an input to the down input of the ramp generator for reversing the direction of the ramp signal to the down direction and wherein the fourth means includes means for detecting the ramp signal in the down direction falling to a predetermined level for producing the cutoff signal.

13. The apparatus of claim 10 and additionally including sixth means responsive to the first means and responsive to the peak voltage and the varying voltage for detecting when the varying voltage decays to a third predetermined percentage of the peak voltage greater than the first predetermined percentage and with the fourth means responsive to the detection by the sixth, second and third means for producing a time delayed cutoff signal in accordance with the time intervals between the detections by the sixth and second means and the second and third means.

14. The apparatus of claim 13 wherein the fourth means includes a composite ramp generator for generating a composite ramp signal in up and down directions in accordance with inputs from the detection by the sixth, second and third means and wherein the fourth means includes means for detecting the ramp signal in the down direction falling to a predetermined level for producing the cutoff signal.

15. A cutoff timer for determining the integration of a signal representative of a time-temperature dilution curve for use in equipment for measuring cardiac output by thermal dilution, the cutoff including first means responsive to the signal representative of the time-temperature dilution curve for determining a time interval on the time-temperature dilution curve in a region of favorable signal-to-noise ratio;

second means responsive to the time interval for determining a time delay as a function of said time interval; and third means responsive to the time delay for stopping the integration at the end of said time delay near the end of the time-temperature curve where the signal is small.

16. The method of terminating the integration of the area under a signal representative of time-temperature dilution curve for use in the measurement of cardiac output by including the following steps, determining a cutoff time for the integration in advance of cutoff in accordance with properties of the signal representative of the time-temperature curve in a region where the signal is large and the signal-to-noise ratio is favorable; and terminating the integration of the area under the signal representative of the time-temperature curve at the predetermined cutoff time, which cutoff time occurs when the signal is small and substantially all of the area under the curve has been directly integrated.

17. The method of terminating the integration as set forth in claim 16 wherein the properties of the signal representative of the time-temperature curve that are used to determine the cutoff time are two time points in said region determined as different percentages of peak temperature and the terminating is at a cutoff time which is a function of the two time points.

18. The method of terminating the integration as set forth in claim 16 wherein the properties of the signal representative of the time-temperature curve are several points on the selected region of the curve and the cutoff time is a function of the several time points.

* * * * *